United States Patent [19]
Bönnemann et al.

[11] Patent Number: 6,090,746
[45] Date of Patent: Jul. 18, 2000

[54] PROCESS FOR PRODUCING TENSIDE-STABILIZED COLLOIDS OF MONO- AND BIMETALS OF THE GROUP VIII AND IB OF THE PERIODIC SYSTEM IN THE FORM OF PRECURSORS FOR CATALYSTS WHICH ARE ISOLABLE AND WATER SOLUBLE AT HIGH CONCENTRATION

[75] Inventors: Helmut Bönnemann, Essen; Werner Brijoux, Oberhausen; Rainer Brinkmann, Mülheim an der Ruhr; Joachim Richter, Karlsruhe, all of Germany

[73] Assignee: Studiengesellschaft Kohle mbH, Mulheim an der Ruhr, Germany

[21] Appl. No.: 08/849,482

[22] PCT Filed: Dec. 7, 1995

[86] PCT No.: PCT/EP95/04803

§ 371 Date: Aug. 29, 1997

§ 102(e) Date: Aug. 29, 1997

[87] PCT Pub. No.: WO96/17685

PCT Pub. Date: Jun. 13, 1996

[30] Foreign Application Priority Data

Dec. 8, 1994 [DE] Germany .............................. 44 43 705

[51] Int. Cl.$^7$ ................. B01J 23/42; B01J 23/02
[52] U.S. Cl. ................. 502/325; 502/339; 502/344; 585/275
[58] Field of Search ....................... 502/173, 325, 502/339, 344; 585/275

[56] References Cited

U.S. PATENT DOCUMENTS 5,147,841  9/1992  Wilcoxon ................. 502/173

*Primary Examiner*—John F. Niebling
*Assistant Examiner*—Alexander G. Ghyka
*Attorney, Agent, or Firm*—Norris, McLaughlin & Marcus, P.A.

[57] ABSTRACT

The invention relates to a process for producing tenside-stabilized colloids of mono- and bimetals of the group VIII and Ib of the periodic system which are isolable in the form of powder and which are soluble at a concentration of at least 10 mg atom of metal/l of water, from metal salts in the presence of strongly hydrophilic tensides with hydrotriorganoborates in THF, or with simple chemical reduction agents like hydrogen or alkali formate in water and alcohols, respectively. Furthermore, the subject matter of the invention is the use of tenside-stabilized colloids which are produced according to this process as precursor for supported catalysts for the selective cis-hydrogenation of C—C triple bonds, for the selective hydrogenation of functional groups at the aromatic nucleus, for the selective hydrogenation of benzene to cyclohexene, for the partial oxidation of the primary alcohol functionality in carbohydrates, as well as for use as a precursor for electrocatalysts in fuel cells.

25 Claims, No Drawings

PROCESS FOR PRODUCING TENSIDE-STABILIZED COLLOIDS OF MONO- AND BIMETALS OF THE GROUP VIII AND IB OF THE PERIODIC SYSTEM IN THE FORM OF PRECURSORS FOR CATALYSTS WHICH ARE ISOLABLE AND WATER SOLUBLE AT HIGH CONCENTRATION

SUMMARY

The invention relates to a process for producing tenside-stabilized colloids of mono- and bimetals of the group VIII and Ib of the periodic system which are isolable in the form of powder and which are soluble at a concentration of at least 100 mg atom of metal/l of water, from metal salts in the presence of strongly hydrophilic tensides with hydrotriorganoborates in THF, or with simple chemical reduction agents like hydrogen or alkali formate in water and alcohols, respectively. Furthermore, the subject matter of the invention is the use of the tenside-stabilized colloids which are produced according to this process as precursor for supported catalysts for the selective cis-hydrogenation of C—C triple bonds, for the selective hydrogenation of functional groups at the aromatic nucleus, for the selective hydrogenation of benzene to cyclohexene, for the partial oxidation of the primary alcohol functionality in carbohydrates, as well as for use as a precursor for electrocatalysts in fuel cells.

DESCRIPTION OF THE PROCESS

The use of colloidally stabilized one- and multi-metallic nanoparticles as separately isolable precursor for producing supported metal catalysts is a new, economically beneficial alternative to the traditional in situ formulation of active metal components on carrier surfaces (H. Bönnemann et al., J. Mol. Catal. 86 (1994), 129–177]. The particular characteristic of the process according to the invention is the pre-formation of colloidally stabilized metal nanoparticles, optionally having an intermetalic composition, with defined size and particle structure. The characteristics of the catalyst (activity, selectivity, lifetime) of such metal colloids which are fixed on carriers are superior to conventional, supported catalysts.

The preferred solvent in this catalyst technology is water, due to economical and ecological reasons. The subject matter of the present invention is a process which permits to stabilize mono- and bimetallic nanoparticles in the form of powder in such a way, that highly concentrated colloidal solutions of the corresponding mono- and bimetallic catalyst-precursor can be produced in water without appreciable metal precipitations. By fixation of the precursor from aqueous solution on organic or inorganic carrier materials, new heterogeneous catalysts are prepared according the invention, for. e.g. selective hydrogenations, partial oxidations, or electrocatalysts for fuel cells.

According to the state of the art, some nanometals can be stabilized colloidally in water [T. Sato, S. Kuroda, A. Takami, Y. Yonezawa, H. Hada, Appl. Organomet. Chem. 1991, 5, 261; T. Sato et al., J. Appl. Phys. 1990, 68,1297; T. Sato et al., J. Chem. Soc., Faraday Trans. 1, 1987, 83,1559; T. Sato, S. Kuroda, A. Takami, Y. Yonezawa, H. Hada, Appl. Organomet. Chem. 1991, 5, 261; J. H. Fendler, "Membrane-Mimetic Approach to Advanced Materials", Springer-Verlag, Berlin, 1994; J. S. Bradley in "Clusters and Colloids", (Ed. G. Schmid), VCH, Weinheim 1994; H. Hirai, Y. Nakao, N. Toshima, Chem. Lett. 1978, 5, 545; M. Ohtaki, M. Komiyama, H. Hirai, N. Toshima, Macromolecules 1991, 24, 5567; N. Toshima et al., J. Phys. Chem., 1991, 95, 7448; N. Toshima, T. Yonezawa, Makromol. Chem., Macromol. Symp., 1992, 59,327; N. Toshima et al., J. Phys. Chem. 1992, 96,9927; K. Torigoe, K. Esumi, Langmuir 1993, 9, 1664; J. S. Bradley et al., Chem. Mater. 1993, 5, 254; H. Hirai, Y. Nakao, N. Toshima, Chem. Lett. 1976, 9,905; M. Ohtaki, M. Komiyama, H. Hirai, N. Toshima, Macromolecules 1991, 24,5567, N. Toshima, M. Ohtaki, T. Teranishi, Reactive Polym. 1991, 15, 135; C. Larpent, F. Brisse-Le Menn, H. Patin, Mol. Catal. 1991, 65, L35; N. Toshima, T. Takahashi, Bull. Chem. Soc. Jpn. 1992, 65, 400–9].

However, the described metal colloids cannot be isolated, and they are soluble in water only at a high dilution. Therefore, they are not suitable as a catalyst precursor.

Some authors could isolate water soluble nanometal colloids in the presence of hydrophilic P- and N-donators [J. S. Bradley in "Clusters-and Colloids", (Ed. G. Schmid), VCH, Weinheim 1994; G. Schmidt, Chem. Rev. 1992, 92, 1709, H. Liu, N. Toshima, J. Chem. Soc., Chem. Commun. 1992, 1095; C. Amberger, Ber. 1904, 37,124; C. Paal, C. Amberger, Ber. 1905, 38,1398].

Since P- and N-donators, being Lewis bases, give defined metal complex compounds with transition metals which, as is generally known, affects the catalytic efficiency of metals, the use of the mentioned complexing agent for the production of water soluble catalyst precursors is not suitable in the meaning of the present invention. Furthermore, the synthesis of these complexing agents occurs in several steps, and it is uneconomical.

Suitable auxiliary agents are known for stabilizing nanometals in water. Referring to this, also surface-active agents (tensides) were proposed by some authors [H. G. Petrow and R. J. Allen (Prototech Company), U.S. Pat. No. 4,044,193 (1977); G. V. Lisichkin, A. Ya. Yuffa and V. Yu. Khinchagashvii, Russ. J. Phys. Chem., 50 (1976) 1285; V. M. Deshpande, P. Singh and C. S. Narasimhan, J. Mol. Cat., 53 (1989) L21; V. M. Deshpande, P. Singh and C. S. Narasimhan, J. Mol. Cat., 63 (1990) L5; V. M. Deshpande, P. Singh and C. S. Narasimhan, J. Chem. Soc., Chem. Commun., 1990, 1181; Y. Nakao and K. Kaeriyama, J. Coll. and Surf. Sci., 110(l) (1986) 82; C. Larpent, F. Brisse-Le Menn und H. Patin, New J. Chem. 15 (1991) 361; K. Esumi, M. Shiratori, H. Ihshizuka, T. Tano, K. Torigoe and K. Meguro, Langmuir 7 (1991) 457; N. Toshima, T. Takahashi und H. Hirai, Chemistry Letters, 1985, 1245; N. Toshima and T. Takahashi, Chemistry Letters, 1988, 573; J. Kiwi and M. Grätzel, J. Am. Chem. Soc. 101 (1979), 7214]. However, the colloidal solutions of the corresponding metals in water are only stable at an extremely low concentration, not isolable and therefore, are discarded from the beginning as being used according to the invention as precursors for technical catalysts.

A significant progress in the production of water soluble metal colloids received Reetz and Helbig [M. T. Reetz, W. Helbig, J.Am.Chem.Soc. 1994, 116, 7401] by use of a LiCl salt of the sulfobetaine 3-(dimethyldodecyl-ammonio) propane sulfonate in an electrochemical reduction process. According to this electro-chemical process, e.g., a good water soluble palladium colloid which is stabilized with sulfobetaine having a size of 8 nm, was isolated.

An economical alternative to the electrochemical production of nanometals is the chemical reduction of metal salts [H. Bönnemann et al.,Angew. Chem. Int. Ed. Engl. 29 (1990), 273; H. Bönnemann et al., J. Mol. Catal. 86 (1994), 129–177].

The use of commercial tensides for the stabilization of chemically-reductively produced nanometal colloids in highly concentrated aqueous solution could not be learned from the state of the art and from the ruling doctrine. On the contrary, surface-active substances are considered as auxiliary agents for the precipitation of metals from aqueous solution. Surprisingly, it was found now that the chemical reduction of metal salts in the presence of extremely hydrophilic tensides leads to isolable nanometal colloids which form in an amount of at least 100 mg atom metal/l long-term stable solutions in water. The advantage according to the invention of extremely water soluble tensides for the stabilization of colloids illustrates the following comparison: Whereas the poor water soluble tenside $C_{16}H_{33}Me_3NBr$ (solubility according to Fluka catalogue 1993/94, CAS No. 57-09-0=0,1 mole/l of water) does not allow a stabilization of metal colloids in water according to the state of the art [G. V. Lisichkin, A. Ya. Yuffa and V. Yu. Khinchagashvii, Russ. J. Phys. Chem., 50 (1076), 1285], the use according to the invention of 3-(dimethyldodecyl-ammonium)propane sulfonate (solubility according to Fluka catalogue 1993/94, CAS No. 14933-08-5=1,2 mole/l of water) results in a solubility of the stable metal colloids of at least 100 mg atom/l of water.

Inorganic or organic salts of one or more metals from the groups VIII and Ib of the periodic system are dissolved, respectively suspended, in water or in a strongly solvated organic solvent (ether, THF, alcohols) in the presence of an extremely hydrophilic tenside, and they are reacted between 0° C. and 100° C. at environmental pressure, optionally by addition of alkali carbonate, with chemical reduction agents. Such reduction agents are, e.g., hydrogen, alkali formate, complex hydrides and other materials which are technically available for the reduction. The selection of the reducing agent will be determined, respectively, according to the reducing capacity which is necessary for the respective metal salt, as well as according to the stability of the used reagents in protic/aprotic solvents. As the extremely hydrophilic tensides, according to the invention, the following hydrophilic types of tensides can be used for the chemically-reductive preparation of colloids of mono- and bimetals of the groups VIII and Ib of the periodic system in the form of isolable powders which are water soluble in high concentration (>100 mg atom/l): amphiphilic betaines (A), cationic tensides (B), fatty alcohol-polyglycolether (C), polyoxyethylene-carbohydrate-fatty alkylester (D), anionic tensides (E) and amphiphilic sugar tensides (F).

The metal colloids which are prepared according to the invention as catalyst-precursor can be raised from aqueous solution to organic or inorganic carrier materials (e.g. activated carbon, graphitized carbon black, metal oxides) for the production of technically advantageously mono- and bimetallic heterogeneous catalysts. These heterogeneous catalysts which are prepared according to the invention are suitable for the selective cis-hydrogenation of C—C triple bonds (mono- and bimetallic Pd-colloidal catalysts on A-carbon), the selective hydrogenation of functional groups, as for instance —$NO_2$, at the aromatic nucleus (e.g, mono- and bimetallic Pt-colloid on A-carbon), for the selective hydrogenation of benzene to cyclohexene (e.g., Ru-colloid on $La_2O_3$), for the partial oxidation of the primary alcohol functionality in carbohydrates (e.g., Pd-, Pt-, Pd/Pt-colloids on A-carbon), or as electrocatalysts for fuel cells (e.g., Pt-colloid on graphitized carbon black).

EXAMPLES

The following types of tensides can be used according to the invention for the nanometal stabilization (table 1). The examples illustrate the invention without being limited thereby.

TABLE 1

| hydrophilic type of tenside | name | tenside | name, formula, commercial name |
|---|---|---|---|
| A | amphiphilic betaines | A1 | 3-(N,N-dimethyldodecylammonio)-propane sulfonate (SB12) |
| | | A2 | Lauryldimethyl carboxymethyl-ammonium-betaine, REWO |
| | | A3 | Cocoamidopropyl betaine, DEHYTON K, |
| | | A4 | Cocoamidopropyl betaine, AMPHOLYT JB130, |
| B | cationic tensides | B1 | $Cl^-\ CH_3-\underset{\underset{CH_3}{\mid}}{\overset{\overset{C_{18}H_{37}}{\mid}}{N^+}}-CH_2-\underset{\underset{}{}}{\overset{\overset{OH}{\mid}}{CH}}-\underset{\underset{}{}}{\overset{\overset{Cl}{\mid}}{CH_2}}$ <br><br> QUAB 426 |
| | | B2 | $(RCOCH_2CH_2)_n\overset{\overset{O}{\|}}{\underset{\underset{CH_3}{\mid}}{N^+}}(CH_2CH_2OH)_{3-n}$ <br><br> R = alkyl radical of partially hydrogenated palm grease <br> ESTERQUAT AU35 |
| C | fatty alcohol-polyglycolether | C1 | polyoxyethylene laurylether, BRIJ 35 |
| D | Polyoxyethylene carbohydrate-fatty alkylester | D1 | polyoxyethylene sorbitan monolaurate, TWEEN 20 |

TABLE 1-continued

| hydrophilic type of tenside | name | tenside | name, formula, commercial name |
|---|---|---|---|
| E | anionic tensides | E1 | Na-cocoamidoethyl-N-hydroxyethyl glycinate, DEHYTON G |
| F | amphiphilic sugar tensides | F1 | alkylpolyglycoside, APG 600 |

Tenside-stabilized colloids of metals of the groups VIII and Ib of the periodic system by reduction with alkali $BEt_3H$ in THF (see table 2).

Example 1
Ru-colloid (Table 2, No. 4)

2.43 g (7.23 mmole) 3-(N,N-dimethyldodecylammonium)-propane sulfonate (tenside A1) are suspended under protective gas (argon) in 100 ml THF, and 5.60 ml of a 1,29 molar $LiBEt_3H$ solution in THF is added thereto at 20° C., whereby a clear tenside-reduction agent-solution results. This clear tenside-reduction agent-solution is dropped within 4 h at 40° C. under stirring to a suspension of 0.5 g (2.41 mmole) $RuCl_3$ in 100 ml THF, and stirring is continued for further 16 h at 20° C. A grey-black precipitate and an almost colorless, supernatant solution are formed. After 2 h of settling, the supernatant solution is siphoned off, 5 ml acetone and 100 ml THF are added. It is stirred for about 10 min, and again the precipitate is allowed to settle during 1 h. The supernatant clear solution is siphoned off, and the precipitate is dried in high vacuum ($10^{-3}$ mbar, 40° C., 1 h). 0,65 g Ru-colloid in the form of a black solid having a Ru-content of 12.62% are obtained. Particle size according to TEM (transmission electron microscopy): 1–2 nm.

Physical Characterization

The colloids from experiments No. 5 and 26, table 2, were characterized by means of UV spectroscopy.

The XPS-spectrum of colloid No. 19, table 2 shows metallic platinum. The mean particle size was determined by means of TEM of the following colloids: No. 19: 2 nm; No. 20: 2,8 nm; No. 21: 3,7 nm (table 2).

Tenside-stabilized colloids of bimetals of the groups VIII and Ib of the periodic system by reduction with alkali $BEt_3H$ in THF (see table 3).

Example 2
Pt-Co-colloid (Table 3, No. 3)

2.62 g (7.8 mmole) 3-(N,N-dimethyldodecylammonium)-propane sulfonate (tenside A1) are suspended under protective gas (argon) in 100 ml THF, and 6 ml of a 1,29 molar $LiBEt_3H$ solution in THF is added thereto at 20° C., whereby a clear tenside-reduction agent-solution results. This clear tenside-reduction agent-solution is dropped within 20 h at 20° C. under stirring to a suspension of 0.78 g (2.93 mmole) $PtCl_2$ and 0.13 g (0.98 mmole) $CoCl_2$ in 120 ml THF, and stirring is continued for further 67 h at 20° C. A dark grey-brown precipitate is formed. 10 ml acetone are added, it is stirred for 1 h, and the precipitate is allowed to settle. The supernatant clear solution is siphoned off, and the precipitate is washed twice with 50 ml THF. After drying in high vacuum ($10^{-3}$ mbar, 20° C., 1 h) 2,84 g Pt-Co-colloid in the form of a black solid having a metal content of 17.6% Pt and 1,5% Co is obtained. Particle size according to TEM: 2–6 nm.

Physical Characterization

The colloids from experiments No. 4 and 6, table 3, were characterized by means of UV spectroscopy.

Tenside-stabilized colloids of metals of the groups VIII and Ib of the periodic system by reduction with alkali metal boron hydrides in $H_2O$ and alcohols, respectively (see table 4).

Example 3
Pt-colloid (Table 4, No. 7)

2.7 g (5.3 mmole) $H_2PtCl_6\times6\ H_2O$ and 3.6 g (10.6 mmole) 3-(N,N-dimethyldodecylammonium)propane sulfonate (tenside A1) are dissolved under the protective gas argon in 100 ml $H_2O$, and within 2 h a solution of 1.2 g (31.8 mmole) $NaBH_4$ in 50 ml $H_2O$ are added thereto at 20° C. The resultant deep-black reaction mixture is filtered over a D4 glass frit, and the deep-black clear solution is concentrated in high vacuum ($10^{-3}$ mbar, 40° C.) to dryness. 6.39 g Pt-colloid is yielded in the form of a black solid having a Pt content of 12,1%. Mean particle size according to TEM: 4,6 nm.

Physical Characterization

The colloid from experiment No. 2, table 3, was characterized by means of UV spectroscopy.

Tenside-stabilized colloids of bimetals of the groups VIII and Ib of the periodic system by reduction with alkali metal boron hydrides in $H_2O$ and alcohols, respectively (see table 5).

Example 4
Pt-Cu-colloid (Table 5, No. 1)

1.35 g (2.65 mmole) $H_2PtCl_6\times6\ H_2O$ and 0.11 g (0.66 mmole) $CuCl_2\times H_2O$ are dissolved with 4.3 g (12.7 mmole) 3-(N,N-dimethyldodecylammonium)propane sulfonate (tenside A1) under protective gas (argon) in 100 ml $H_2O$, and within 2 h a solution of 0.38 g (17.0 mmole) $LiBH_4$ in 50 ml $H_2O$ are added thereto at 20° C. The resultant deep-black reaction mixture is filtered over a D4 glass frit, and the deep-black clear solution is concentrated in high vacuum ($10^{-3}$ mbar, 40° C.) to dryness. 7.05 g Pt-Cu-colloid is yielded in the form of a black solid having a metal content of 7.02% Pt and 0,52% Cu. Particle size according to TEM: 2.5–4.5 nm; EDX-analysis: Pt:Cu=1:0.2

Physical Characterization

The particle size of colloid no. 6, table 5 was determined by TEM: 3–5 nm; EDX-analysis: Pt:Ru=1:1.05

Tenside-stabilized colloids of metals of the groups VIII and Ib of the periodic system by reduction with hydrogen in $H_2O$ (see table 6).

Example 5
Pt-colloid (Table 6, No. 15)

1.4 g (5.3 mmole) $PtCl_2$, 7.2 g (21.2 mmole) 3-(N,N-dimethyldodecylammonium)propane sulfonate (tenside A1) and 0.4 g (5.3 mmole) $Li_2CO_3$ are taken up under a protective gas (argon) in 100 ml $H_2O$, and during 3 h a stream of $H_2$ is passed through this mixture at 20° C. A clear black solution is formed after approximately 30 min, from which all volatile matter is separated in high vacuum ($10^{-3}$ mbar, 40° C.). 8.4 g Pt-colloid is yielded in the form of a black solid having a Pt-content of 10.7%. Mean particle size according to TEM: 2.2 nm.

Annotation Relating to Operating the Reaction

Experiment no. 17, table 6—deviating from the description of the above experiments—was performed in air.

Physical Characterization

The colloids from experiment nos. 1, 4, 5 and 6, table 6 were characterized by uv-spectroscopy.

The mean particle size of the following colloids was determined by TEM: no. 10:2.2 nm; no. 11:3.1 nm (table 6).

Tenside-stabilized colloids of bimetals of the groups VIII and Ib of the periodic system by reduction with hydrogen in $H_2O$

Example 6

Pt-Pd-colloid 1.35 g (2.65 mmole) $H_2PtCl_6 \times 6\ H_2O$ and 0,7 g (2.65 mmole) $Pd(NO_3)_2 \times H_2O$ are dissolved together with 7 g polyoxyethyenelaurylether (tenside C1) and 1.0 g (13.25 mmole) $Li_2CO_3$ under a protective gas (argon) in 100 ml $H_2O$, and during 4 h $H_2$ gas is passed through it at 20° C. The resultant deep black reaction mixture is filtered over a D4 glass frit, and the deep-black clear solution is concentrated in high vacuum ($10^{-3}$ mbar, 40° C.) to dryness. 11,2 g Pt-Pd colloid are obtained in the form of a black solid having a metal content of 4.3% Pt and 2.3% Pd.

Tenside-stabilized colloids of bimetals of the groups VIII and Ib of the periodic system by reduction with Li-formate in $H_2O$

Example 7

Pt-Rh-colloid 1.35 g (2.65 mmole) $H_2PtCl_6 \times 6\ H_2O$ and 0,7 g (2.65 mmole) $RhCl_3 \times H_2O$ are dissolved with 7 g polyoxyethylene laurylether (tenside C1) under a protective gas (argon) in 150 ml $H_2O$, and during 20 h a solution of 2.86 g (55.0 mmole) Li-formate in 50 ml $H_2O$ is added thereto at 60° C. The resultant deep black reaction mixture is filtered over a D4 glass frit, and the deep-black clear solution is concentrated in high vacuum ($10^{-3}$ mbar, 40° C.) to dryness. 12.5 g Pt-Rh colloid are obtained in the form of a black solid having a metal content of 4.0% Pt and 2.0% Rh.

Fixation of the carrier

Example 8

Preparation of a Pd-tenside A1/activated Carbon Catalyst for the Partial Oxidation of Carbohydrates (5 Percent Per Weight of Pd/C)

1.254 g of a microporous (<5 nm) powdery active carbon having a grain size of 20 μm are suspended in 50 ml deoxygenated $H_2O$, and 64.7 ml of a solution of Pd-colloid no. 16, table 2 in deoxygenated water (1.02 mg Pd/ml) are given thereto within 16 h under stirring. The covered active carbon is separated over a glas filter frit; yielding a colorless filtrate. It is washed twice with 25 ml deoxygenated water, respectively, and dried during 16 h in vacuum ($10^{-3}$ mbar). Subsequently, the catalyst is oxygenated during 16 h at 0,1 mbar (approximately 0,2% $O_2$). The obtained catalyst can be handled in air.

Example 9

Preparation of a Pd-tenside A1/active Carbon-Catalyst for the Selective Hydrogenation of C≡C (5% Per Weight of Pd/C)

A solution of 0.7885 g (corresponding to 0.1053 g Pd) colloid no. 16, table 2 in 40 ml distilled water is dropped within 16 h under argon to 2.00 activated carbon (Degussa carrier material 101, charge 514) which was given in the form of a suspension in 40 ml water under argon. Thereby, the colloid is completely absorbed on the activated carbon which can be seen by the decoloration of the solution. The catalyst is filtered off, dried during 16 h at 20° C. in high vacuum ($10^{-3}$ mbar), and it is oxygenated during 16 h at 20° C. at 0.1 mbar (approximately 0.2% $O_2$).

Example 10

Preparation of a Ru-tenside A1/lanthanumoxid Catalyst for the Selective Hydrogenation of Benzene (1 Percent Per Weight of $Ru/La_2O_3$)

5.505 g $La_2O_3$ (BET surface area of 59 $m^2/g$) are suspended in 100 ml deoxygenated $H_2O$ under a protective gas. Within 30 min 50 ml of a solution of Ru-colloid no.4, table 2 in deoxygenated $H_2O$ (440 mg, EA: 12.62% Ru), is dropped thereto. Thereby, the white oxidic carrier changes to a grey colour. The complete absorption can be seen from the decoloration of the black solution. The coated carrier is allowed to settle completely, and the supernatant, clear aqueous solution is siphoned off. After drying in vacuum ($10^{-3}$ mbar, 3 h), a grey powder is obtained which is stable in air.

Catalysis

Example 11

Use of a Pd-catalyst for the Oxidation of Glucose to Gluconic Acid 100 ml of an aqueous solution of glucose with 16 g glucose (99 percent per weight) (88 mmole) and 0.24 g of the catalyst described in example 8 (1.5 percent per weight in relation to the amount of glucose) are transferred to a 250 ml stirring reactor equipped with gassing stirrer, thermometer, alkali metering, pH electrode and oxygen feeding. The oxygen is distributed at normal pressure by means of the gassing stirrer in the solution at a reaction temperature of 56° C. The resulting gluconic acid is neutralized by dropping 10 percent per weight of caustic soda thereto. Thereby, the pH value of the suspension is 10.0. The catalyst is filtered off, and the filtrate is analyzed by means of ion chromatography and HPLC.

Conversion (min): 49%

Selectivity (120 min): 92%

Activity (120 min): 327 g [gluconic acid]/g [Pd]×hour

Example 12

Use of a Pd-catalyst for the Selective Hydrogenation of 3-hexyne-1-ol to Cis-3-hexene-1-ol 30.0 mg of a Pd-colloid/activated carbon catalyst, prepared according to example 9, are weighed in a 100 ml dropping funnel. The measuring of the selectivity is performed in a reactor which is thermostatted to −10° C. The dropping funnel is put upon the reactor, the whole apparatus is evacuated several times and flushed with hydrogen. Subsequently, the catalyst is placed into the reactor in hydrogen-counterflow with 100 ml of absolute, non-degenerated ethanol under argon in 2 portions of 50 ml, respectively. The dropping funnel is taken off and it is replaced by a septum. 10 ml 3-hexyne-1-ol are injected through the septum. After thermostatting the suspension at −10° C. and pressure compensation, the path to a 1 l-precision buret which is sealed by mercury is opened. GC samples are taken through the septum by means of a syringe with filter aid and hypodermic steel needle in regular intervals until stoichiometric hydrogen take-up is attained. Selectivity according to GC: 94.9%.

Example 13
Use of a Ru-catalyst for the Partial Hydrogenation of Benzene to Cyclohexene 10 ml benzene, 40 ml water with 3 g NaOH and 500 mg of the catalyst described in example 10 (1 percent per weight Ru/$La_2O_3$, 6.25 percent per weight of catalyst in relation to the amount of benzene) are filled into a 100 ml stainless steel autoclave. The content is stirred with the club stirrer and heated to 150° C. Now, it is pressed on to 50 bar of hydrogen pressure. The autoclave is taken from the heating jacket support after 30 min, and stirring is interrupted. Thereby, a hydrogen up-take of 18 bar can be noticed. The residual $H_2$ pressure is blown off after cooling, and a sample is taken from the upper organic phase which is examined by gas chromatography.

Conversion(benzene): 8.5%
Selectivity (cyclohexene): 78.5%.

Example 14
Preparation of a Platinum Colloid Stabilized by Dihydrocinchonidine 0.104 g $PtCl_4$ (0.31 mmole) are dissolved in a 100 ml two-neck flask, provided with reflux condenser and a septum, in 83 ml water, and heated to reflux temperature in an oil bath. The temperature of the oil bath is 140° C. (±5° C.) during the synthesis. A solution of 0.092 g dihydrocinchonidine (0.31 mmole) in 7 ml of 0.1 n formic acid is rapidly injected through the septum. In the beginning, the reaction mixture becomes turbid and begins to become black colored after some minutes. The reaction is finished approximately ten minutes after the beginning of the black coloration. The reaction mixture is frozen in liquid nitrogen and liberated of water and the forming hydrochloric acid by freeze drying. A black powder is obtained which can be completely dispersed in water. If the formed platinum colloids should be applied on carrier materials, the aqueous product dispersion can be used without isolation of the metal particles before the application on the carrier. The yield is 0.18 g (103% of the theory) in this reaction. The elemental analysis shows 34.5% Pt, 16% Cl, 39.5% C, 5% H and 5% N. Electron-microscopic examinations show an average particle size of 2 nm.

Example 15
Preparation of a Heterogeneous Platinum Catalyst by Adsorption of Platinum Colloids on Silicon Dioxide and Active Carbon 100 ml of the colloid, described in example 14, are directly taken up after the synthesis in 100 ml cold, distilled water, and are dropped during one hour to 100 ml of the carrier suspension. Either the highly disperse silicon dioxide Aerosil P 25™ (Degussa) or the active carbon carrier 196 (Degussa) which was oxidized with sodium hypochloride before the application to the carrier, can be used as carriers. The obtained suspensions are stirred with a magnetic stirrer at a low rotational speed during two days, and they are susequently filtrated. The filtrate is completely discolored, a fact from which it can be concluded that the metal colloids were quantitatively absorbed on the carrier. The thus obtained heterogeneous platinum catalysts were dried in a drying oven, and they can be used subsequently as hydrogenation catalysts without further intermediary step. A uniform and agglomeration-free distribution of the colloids on the carrier materials could be proven by electron-microscopic examinations.

Example 16
Enantioselective Hydrogenation of 2-keto-propane Acid Ethylester to 2-hydroxy-propane Acid Ethylester A 100 ml autoclave is charged with the catalyst described in example 15 (platinum on silicon dioxide; metal content 5%), 5 ml 2-keto-propane acid ethylester (45 mmole), 20 ml dihydrocinchonidine (0.1 mmole), 10 ml acetic acid and a magnetic stirrer nucleous having a size of 3 cm. The presure vessel is degassed after being closed, and subsequently, 100 bar hydrogen are pressed on under vigorous stirring. The reaction takes place at 20° C., and it is terminated approxiamtely after 15 minutes. Following the expansion of the pressure vessel, the product mixture is liberated of the catalyst by filtration, the clear filtrate is taken up in 180 ml saturated sodium bicarbonate solution and subsequently extracted three times with each 20 ml of diethyl ether. The combined organic phases are concentrated on a rotary evaporator, the remaining clear solution is examined by NMR spectroscopy and mass spectroscopy, and it is identified as 2-hydroxy-propane acid ethylester. The yield was determined by gas chromatography to 90%. The optical yield of the reaction was examined by gas chromatography on a chiral column, and yields an excess of enantiomer of 81%.

TABLE 2

Tenside stabilized colloids of metals of the groups VIII-Ib of the periodic system by reduction with alkali $BEt_3H$ in THF

| No. | Metal salt g/mmole | Tenside g/mmole | Metal salt/-tenside molar ratio | Reduction agent mmole | Solvent ml | Reduction conditions T, °C. t, h | isolated amount of product g | Metal content % | Water solubility in mg atom metal/l water |
|---|---|---|---|---|---|---|---|---|---|
| 1 | $NiBr_2$ 0,7/5,3 | C1 7/- | — | $LiBEt_3H$ 10,6 | THF 200 | 50 20 | 8,5 | Ni: 2,9 | 110 |
| 2 | $CoCl_2$ 0,7/5.3 | C1 7/- | — | $LiBEt_3H$ 10,6 | THF 200 | 50 20 | 8,3 | Co: 3,1 | 120 |
| 3 | $CuCl_2$ 0,71/5,3 | A1 7,2/21,2 | 1:4 | $LiBEt_3H$ 10,6 | THF 500 | 20 48 | 9,02 | Cu: 3,5 | 300 |
| 4 | $RuCl_3$ 0,5/2,41 | A1 2,43/7,23 | 1:3 | $LiBEt_3H$ 7,23 | THF 200 | 40 4 | 0,65 | Ru: 12,62 | 310 |
| 5 | $RuCl_3$ 0,21/1,04 | A2 0,85/3,13 | 1:3 | $LiBEt_3H$ 3,13 | THF 100 | 40 2 | 0,23 | Ru: 13,52 | 150 |
| 6 | $RhCl_3$ 2,05/9,7 | A1 9,86/29,38 | 1:3 | $LiBEt_3H$ 30,78 | THF 600 | 65 28 | 3,9 | Rh: 25,21 | 320 |
| 7 | $RhCl_3$ 0,45/2,15 | A1 1,443/4,3 | 1:2 | $LiBEt_3H$ 6,45 | THF 105 | 40 34 | 1,91 | Rh: 11,50 | 350 |
| 8 | $RhCl_3$ 0,45/2,15 | A1 0,721/2,15 | 1:1 | $LiBEt_3H$ 6,45 | THF 105 | 40 34 | 1,08 | Rh: 20,4 | 370 |
| 9 | $RhCl_3$ | A1 | 1:0,75 | $LiBEt_3H$ | THF | 40 34 | 0,87 | Rh: 25,2 | 410 |

TABLE 2-continued

Tenside stabilized colloids of metals of
the groups VIII-Ib of the periodic system by reduction with alkali BEt$_3$H in THF

| No. | Metal salt g/mmole | Tenside g/mmole | Metal salt/-tenside molar ratio | Reduction agent mmole | Solvent ml | Reduction conditions T, °C. | t, h | isolated amount of product g | Metal content % | Water solubility in mg atom metal/l water |
|---|---|---|---|---|---|---|---|---|---|---|
| 10 | RhCl$_3$ 0,45/2,15 | A1 0,541/1,61 | 1:0,5 | LiBEt$_3$H 6,45 | THF 105 | 40 | 34 | 0,67 | Rh: 32,9 | 440 |
| 11 | RhCl$_3$ 0,45/2,15 | A2 0,361/1,075 | 1:3 | LiBEt$_3$H 6,45 | THF 120 | 60 | 16 | 2,0 | Rh: 10,1 | 180 |
| 12 | RhCl$_3$ 0,45/2,15 | A2 1,745/6,45 | 1:2 | LiBEt$_3$H 6,45 | THF 120 | 60 | 16 | 1,60 | Rh: 13,1 | 170 |
| 13 | RhCl$_3$ 0,45/2,15 | A2 1,164/4,3 | 1:3 | LiBEt$_3$H 6,45 | THF 120 | 60 | 16 | 2,0 | Rh: 10,1 | 140 |
| 14 | RhCl$_3$ 0,45/2,15 | A3 1,745/6,45 | 1:2 | LiBEt$_3$H 6,45 | THF 120 | 60 | 16 | 1,30 | Rh: 16,2 | 110 |
| 15 | PdCl$_2$ 0,71/4 | A2 0,855/4,3 | 1:2 | LiBEt$_3$H 5,6 | THF 300 | 25 | 16 | 2,64 | Pd: 14,8 | 160 |
| 16 | PdCl$_2$ 1,37/7,75 | A1 2,17/8 | 1:2 | LiBEt$_3$H 10,8 | THF 500 | 25 | 16 | 3,13 | Pd: 13,35 | 280 |
| 7 | PdCl$_2$ 0,71/4 | A1 5,2/15,5 | 1:2 | LiBEt$_3$H 5,6 | THF 300 | 25 | 24 | 2,99 | Pd: 13,7 | 260 |
| 8 | IrCl$_3$ 0,51/1,71 | A1 2,68/8 | 1:3 | LiBEt$_3$H 5,16 | THF 100 | 60 | 16 | 2,10 | Ir: 8,99 | 370 |
| 9 | PtCl$_2$ 2,74/10,3 | A1 1,72/5,13 | 1:2 | LiBEt$_3$H 20,69 | THF 1100 | 20 | 24 | 1,96 | Pt: 58,93 | 420 |
| 20 | PtCl$_2$ 1,03/3,87 | A1 6,94/20,68 | 1:1 | LiBEt$_3$H 7,74 | THF 240 | 20 | 27 | 1,6 | Pt:32,64 | 350 |
| 21 | PtCl$_2$ 1,03/3,87 | A1 1,31/3,9 | 1:0,5 | LiBEt$_3$H 7,74 | THF 240 | 20 | 27 | 1,46 | Pt: 51,50 | 320 |
| 22 | PtCl$_2$ 5,5/20,67 | A2 0,655/1,95 | 1:2 | LiBEt$_3$H 41,7 | THF 1200 | 25 | 16 | 16,24 | Pt: 22,09 | 160 |
| 23 | PtCl$_2$ 0,133/0,5 | A2 11,3/41,7 | 1:1 | LiBEt$_3$H 1,0 | THF 80 | 20 | 16 | 0,43 | Pt: 22,6 | 170 |
| 24 | PtCl$_2$ 0,133/0,5 | A2 0,138/0,5 | 1:0,5 | LiBEt$_3$H 1,0 | THF 80 | 20 | 16 | 0,35 | Pt: 27,7 | 180 |
| 25 | PtCl$_2$ 0,857/3,23 | A3 0,068/0,25 | 1:2 | LiBEt$_3$H 6,45 | THF 200 | 20 | 108 | 2.0 | Pt: 19,60 | 110 |
| 26 | AgBr 1,36/5,1 | A1 2,35/6,45 | 1:2 | LiBEt$_3$H 10,2 | THF 550 | 20 | 24 | 2.82 | Ag: 11,52 | 130 |

TABLE 3

Tenside-stabilized colloids of bimetals of the groups VIII-Ib of the
periodic system by reduction with alkali BEt$_3$ H in THF

| No. | Metal salt g/mmole | Tenside g/mmole | Metal salt/-tenside molar ratio | Reduction agent mmole | Solvent ml | Reaction conditions T, °C. | t,h | isolated amount of product g | Metal content % | Water solubility in mg atom metal/l water |
|---|---|---|---|---|---|---|---|---|---|---|
| 1 | RuCl$_3$—FeCl$_3$ 0,5/2,41 - 0,039/0,24 | A1 2,67/7,95 | 1:3 | LiBEt$_3$H 7,95 | THF 200 | 60 | 4 | 2,60 | Ru: 8,84 Fe: 0,38 | 210 |
| 2 | RuCl$_3$—FeCl$_3$ 0,5/2,41 - 0,078/0,48 | A1 2,91/8,67 | 1:3 | LiBEt$_3$H 8,67 | THF 200 | 60 | 4 | 2,45 | Ru: 8,52 Fe: 0,71 | 170 |
| 3 | PtCl$_2$—CoCl$_2$ 0,78/2,93 - 0,13/0,98 | A1 2,62/7,8 | 1:2 | LiBEt$_3$H 7,74 | THF 220 | 20 | 20 | 2,84 | Pt: 17,6 Co: 1,5 | 280 |
| 4 | PtCl$_2$—CoBr$_2$ 0,66/3,23 - 0,7/3,2 | A2 3,5/12,9 | 1:2 | LiBEt$_3$H 12,9 | THF 300 | 20 | 20 | 4,18 | Pt: 12,4 Co: 3,75 | 200 |
| 5 | PtCl$_2$—CoBr$_2$ 0,86/3,23 - 0,08/0,36 | A2 1,95/7,18 | 1:2 | LiBEt$_3$H 7,2 | THF 300 | 20 | 20 | 3,1 | Pt: 20,1 Co: 0,68 | 210 |
| 6 | CODPtCl$_2$—CoBr$_2$ 0,6/1,6 - 0,35/1,61 | A2 1,75/6,45 | 1:2 | LiBEt$_3$H 6,45 | THF 300 | 20 | 20 | 1,92 | Pt: 14,5 Co: 4,4 | 190 |
| 7 | PtCl$_2$—NiBr$_2$ 0,68/3,23 - 0,08/0,36 | A2 1,97/7,18 | 1:2 | LiBEt$_3$H 7,2 | THF 360 | 20 | 20 | 3,0 | Pt: 20,9 Ni: 0,7 | 185 |
| 8 | PtCl$_2$—RhCl$_3$ 2,31/8,72 - 0,61/2,91 | A1 8,78/26,17 | 1:2,25 | LiBEt$_3$H 26,16 | THF 1200 | 40 | 24 | 2,66 | Pt: 43,6 Rh: 7,55 | 405 |
| 9 | PtCl$_2$—RhCl$_3$ 1,80/6,79 - 1,41/6,74 | A1 11,56/34,45 | 1:2,55 | LiBEt$_3$H 34,0 | THF 1100 | 50 | 28 | 3,60 | Pt: 25,0 Rh: 11,1 | 380 |
| 10 | PtCl$_2$—RhCl$_3$ | A1 | 1:2,8 | LiBEt$_3$H | THF | 60 | 24 | 4,4 | Pt: 13,89 | 370 |

TABLE 3-continued

Tenside-stabilized colloids of bimetals of the groups VIII-Ib of the periodic system by reduction with alkali $BEt_3H$ in THF

| No. | Metal salt g/mmole | Tenside g/mmole | Metal salt/-tenside molar ratio | Reduction agent mmole | Solvent ml | Reaction conditions T, °C. | t,h | isolated amount of product g | Metal content % | Water solubility in mg atom metal/l water |
|---|---|---|---|---|---|---|---|---|---|---|
| 11 | $PtCl_2$—$PdCl_2$ 0,88/3,32 - 2,76/13,18 1,03/3,88 - 0,68/3,88 | A1 15,5/46,19 5,2/15,5 | 1:2 | $LiBEt_3H$ 46,17 15,5 | THF 1200 550 | 20 | 24 | 5,13 | Rh: 16,3 Pt: 8,42 Pd: 4,45 | 350 |
| 12 | $PtCl_2$—$IrCl_3$ 3,99/15,0 - 0,49/1,67 | A1 11,74/35,0 | 1:2.1 | $LiBEt_3H$ 35,0 | THF 1200 | 60 | 16 | 16,03 | Pt: 17,3 Ir: 1,87 | 430 |
| 13 | $PtCl_2$—$IrCl_3$ 1,86/7,0 - 2,09/7,0 | A1 11,74/35,0 | 1:2,5 | $LiBEt_3H$ 35,0 | THF 1200 | 60 | 16 | 14,4 | Pt: 8,8 Ir: 8,6 | 410 |
| 14 | $PtCl_2$—$IrCl_3$ 0,37/1,4 - 3,76/12,6 | A1 13,62/40,6 | 1:2,9 | $LiBEt_3H$ 66,4 | THF 1200 | 60 | 64 | 18,22 | Pt: 1,4 Ir: 13,0 | 400 |
| 15 | $PtCl_2$—$IrCl_3$ 3,99/15,0 - 0,49/1,67 | A2 9,48/35,0 | 1:2,1 | $LiBEt_3H$ 39,5 | THF 660 | 60 | 16 | 10,65 | Pt: 15,3 Ir: 1,6 | 190 |

TABLE 4

Tenside-stabilized colloids of metals of the groups VIII-Ib of the periodic system by reduction with alkali metal boron hydrides in $H_2O$ and alcohols, respectively

| No. | Metal salt g/mmole | Tenside g/mmole | Metal salt/-tenside molar ratio | Reduction agent mmole | Solvent ml | Reactions conditions T, °C. | t,h | isolated amount of product g | Metal content % | Water solubility in mg atom metal/l water |
|---|---|---|---|---|---|---|---|---|---|---|
| 1 | $RuCl_3 \times H_2O$ 0,36/1,74 | A1 - $NH_4Cl$ 1,75/5,21 - 0,28/5,21 | 1:3 | $NaBH_4$ 0,2/5,21 | $H_2O$ 150 | 40 | 2 | 1,24 | Ru: 7,65 | 430 |
| 2 | $RuCl_3 \times H_2O$ 0,31/1,17 | A1 - $NH_4Cl$ 1,18/3,51 - 0,19/3,51 | 1:3 | $LiBH_4$ 0,08/3,51 | $H_2O$ 160 | 40 | 2 | 0,42 | Ru: 9,87 | 425 |
| 3 | $RhCl_3 \times 3H_2O$ 0,30/1,43 | A1 - $NH_4Cl$ 1,44/4,3 - 0,23/4,3 | 1:3 | $NaBH_4$ 0,17/4,3 | $H_2O$ 100 | 20 | 2 | 1,14 | Rh: 8,25 | 450 |
| 4 | $RhCl_3 \times H_2O$ 1,4/5,3 | A1 7,2/21,2 | 1:4 | $LiBH_4$ 0,34/15,9 | Ethanol 150 | 0 | 24 | 7,3 | Rh: 5,5 | 110 |
| 5 | $RiCl_2$ 0,126/0,48 | A1 0,669/1,99 | 1:4 | $NaBH_4$ 0,037/1,0 | $H_2O$ 80 | 20 | 24 | 0,92 | Pt: 9,8 | 355 |
| 6 | $PiCl_2$ 1,4/5,3 | A1 - $NH_4Cl$ 3,6/10,8 - 0,4/7,9 | 1:2 | $NaBH_4$ 0,4/10,6 | $H_2O$ 100 | 20 | 3 | 4,8 | Pt.: 20,2 | 360 |
| 7 | $H_2PtCl_6 \times 6H_2O$ 2,7/5,3 | A1 3,6/10,6 | 1:2 | $NaBH_4$ 1,2/31,8 | $H_2O$ 150 | 20 | 2 | 6,39 | Pt: 12,1 | 320 |
| 8 | $H_2PtCl_6 \times 6H_2O$ 2,7/5,3 | A1 7,2/21,2 | 1:4 | $LiBH_4$ 1,2/31,8 | Ethanol 150 | 0 | 24 | 8,1 | Pt: 9,5 | 120 |

TABLE 5

Tenside-stabilized colloids of bimetals of the groups VIII-Ib of the periodic system by reduction with alkali metal boron hydrides in $H_2O$ and alcohols, respectively

| No. | Metal salt g/mmole | Tenside g/mmole | Metal salt/-tenside molar ratio | Reduction agent mmole | Solvent ml | Reaction conditions T, °C. | t,h | isolated amount of product g | Metal content % | Water solubility in mg atom metal/l water |
|---|---|---|---|---|---|---|---|---|---|---|
| 1 | $H_2PtCl_6$—$CuCl_2 \times H_2O$ 1,35/2,65 - 0,11/0,66 | A1 4,3/12,7 | 1:3,84 | $LiBH_4$ 0,38/17,0 | $H_2O$ 150 | 20 | 2 | 7,05 | Pt: 7,02 Cu: 0,52 | 390 |
| 2 | $H_2PtCl_6$—$CuCl_2 \times H_2O$ 1,35/2,65 - 0,05/0,295 | A2 6,4/23,6 | 1:8 | $LiBH_4$ 0,38/17 | $H_2O$ 150 | 20 | 2 | 8,5 | Pt: 6,0 Cu: 0,2 | 170 |
| 3 | $RhCl_3 \times H_2O$—$IrCl_3 \times H_2O$ 0,7/2,65 - 08/2,65 | A1 7,2/21,2 | 1:4 | $LiBH_4$ 0,3/13,25 | $H_2O$ 200 | 20 | 2 | 7,06 | Rh: 2,7 Ir: 5,0 | 340 |
| 4 | $RhCl_3 \times 3H_2O$—$RuCl_3 \times H_2O$ 0,7/2,65 - 0,7/2,65 | A1 7,2/21,2 | 1:4 | $LiBH_4$ 0,35/15,9 | $H_2O$ 200 | 20 | 2 | 10,52 | Rh: 2,3 Ru: 2,3 | 410 |
| 5 | $RuCl_3 \times H_2O$—$IrCl_3 \times H_2O$ 0,7/2,65 - 0,8/2,65 | A1 7,2/21,2 | 1:4 | $LiBH_4$ 0,35/15,9 | $H_2O$ 200 | 20 | 2 | 8,7 | Ru: 2,3 Ir: 4,9 | 450 |
| 6 | $H_2PtCl_6$—$RuCl_3 \times H_2O$ 1,35/2,65 - 0,7/2,65 | A1 7,2/21,2 | 1:4 | $LiBH_4$ 0,53/23,85 | $H_2O$ 200 | 20 | 2 | 10,36 | Pt: 4,5 Ru: 2,2 | 380 |
| 7 | $H_2PtCl_6$—$RuCl_3 \times H_2O$ | A1 7,2/21,2 | 1:4 | $LiBH_4$ | Ethanol | 0 | 24 | 8,02 | Pt: 4,7 | 120 |

TABLE 5-continued

Tenside-stabilized colloids of bimetals of the groups VIII-Ib of the periodic system by reduction with alkali metal boron hydrides in H₂O and alcohols, respectively

| No. | Metal salt g/mmole | Tenside g/mmole | Metal salt/-tenside molar ratio | Reduction agent mmole | Solvent ml | Reaction conditions T, °C. | t,h | isolated amount of product g | Metal content % | Water solubility in mg atom metal/l water |
|---|---|---|---|---|---|---|---|---|---|---|
| 8 | H₂PtCl₆—RhCl₃ × H₂O 1,35/2,65 - 0,7/2,65 | A1 7,2/21,2 | 1:4 | NaBH₄ 0,53/23,85 0,9/23,85 | H₂O 200 200 | 20 | 2 | 12,1 | Ru: 2,3 Pt: 4,3 Rh: 2,0 | 360 |
| 8 | H₂PtCl₆—RhCl₃ × H₂O 1,35/2,65 - 0,7/2,65 | A1 7,2/21,2 | 1:4 | LiBH₄ 0,53/23,85 | H₂O 200 | 20 | 2 | 10,58 | Pt: 4,5 Rh: 2,2 | 355 |
| 10 | H₂PtCl₆—PdCl₂ × 2H₂O 1,35/2,65 - 1,0/2,65 | A1 7,2/21,2 | 1:4 | LiBH₄ 0,47/21,2 | H₂O 150 | 20 | 2 | 11,1 | Pt: 4,5 Pd: 2,5 | 310 |
| 11 | H₂PtCl₆—Pd(NO₃)₂× H₂O 0,55/1,06 - 1,1/4,24 | C1 7,0/— | | LiBH₄ 0,33/14,8 | H₂O 150 | 20 | 2 | 10,2 | Pt; 2,0 Pd: 4,3 | 140 |
| 12 | H₂PtCl₆—IrCl₃ × H₂O 1,35/2,65 - 0,8/2,65 | A1 7,2/21,2 | 1:4 | LiBH₄ 0,47/21,2 | H₂O 200 | 20 | 2 | 10,34 | Pt: 4,3 Ir: 4,4 | 400 |
| 13 | H₂PtCl₆—IrCl₃ × H₂O 1,35/2,65 - 0,8/2,65 | A1 7,2/21,2 | 1:4 | LiBH₄ 0,53/23,85 | H₂O 200 | 20 | 2 | 10,2 | Pt: 4,4 Ir: 4,5 | 420 |

TABLE 6

Tenside-stabilized colloid of metals of the groups VIII-Ib of the periodic system by reduction with hydrogen in H₂O

| No. | Metal salt g/mmole | Tenside g/mmole | Metal salt/-tenside molar ratio | Reduction agent | Solvent ml | Reaction conditions T, °C. | t,h | P,bar | isolated amount of product g | Metal content % | Water solubility in mg atom metal/l water |
|---|---|---|---|---|---|---|---|---|---|---|---|
| 1 | RuCl₃ × H₂O 0,25/0,95 | A1 0,96/2,89 | 1:3 | H₂ | H₂O 100 | 60 | 10 | 1 | 0,43 | 10,98 | 370 |
| 2 | RuCl₃ 0,16/0,78 | A1 0,79/2,34 | 1:3 | H₂ | H₂O 100 | 60 | 18 | 50 | 0,22 | 9,41 | 375 |
| 3 | RuCl₃ × H₂O 0,22/0,84 | A2-K₂CO₃ 0,68/2,53 - 0,23/1,67 | 1:3 | H₂ | H₂O 80 | 60 | 3 | 1 | 0,38 | 7,1 | 160 |
| 4 | Ru₂(OAc)₄ 0,27/0,62 | A1 1,25/3,7 | 1:8 | H₂ | H₂O 100 | 80 | 16 | 50 | 0,41 | 8,78 | 210 |
| 5 | Ru(Acac)₃ 0,39/0,97 | A1 0,98/2,91 | 1:3 | H₂ | H₂O 100 | 60 | 16 | 50 | 0,35 | 9,37 | 340 |
| 6 | RhCl₃ × H₂O 0,42/1,6 | A1 1,62/4,81 | 1:3 | H₂ | H₂O 60 | 20 | 2 | 1 | 1,02 | 11,40 | 330 |
| 7 | RhCl₃ × H₂O 0,40/1,52 | A2 1,24/4,57 | 1:3 | H₂ | H₂O 100 | 20 | 2 | 1 | 0,85 | 10,73 | 150 |
| 8 | PdBr₂ 1,4/5,3 | A1-Li₂CO₃ 7,2/21,2 - 0,4/5,3 | 1:4 | H₂ | H₂O 100 | 20 | 3 | 1 | 9,6 | 5,3 | 290 |
| 9 | H₂PtCl₆ × 6 H₂O 2,7/5,3 | A1 - Na₂CO₃ 7,2/21,2 - 3,4/31,8 | 1:4 | H₂ | H₂O 100 | 20 | 4 | 1 | 12,6 | 7,1 | 360 |
| 10 | PtCl₂ 1,4/5,3 | A1 - K₂CO₃ 7,2/21,2 - 0,73/5,3 | 1:4 | H₂ | H₂O 100 | 20 | 1,5 | 1 | 8,79 | 9,7 | 330 |
| 11 | PtCl₂ 1,4/5,3 | A1 - K₂CO₃ 7,2/21,2 - 0,73/5,3 | 1:4 | H₂ | H₂O 100 | 20 | 3 | 1 | 8,5 | 10,1 | 310 |
| 12 | PtCl₂ 1,4/5,3 | A1 - Na₂CO₃ 7,2/21,2 - 0,56/5,3 | 1:4 | H₂ | H₂O 100 | 20 | 1,5 | 1 | 9,0 | 10,8 | 350 |
| 13 | PtCl₂ 21/79,5 | A1 - Li₂CO₃ 108/318 - 6/79,5 | 1:4 | H₂ | H₂O 1500 | 20 | 2 | 1 | 140 | 10,3 | 370 |
| 14 | PtCl₂ 21/79,5 | A1 - Li₂CO₃ 54/159 - 3/39,75 | 1:2 | H₂ | H₂O 1500 | 20 | 2 | 1 | 73,7 | 17,9 | 450 |
| 15 | PtCl₂ 1,4/5,3 | A1 - Li₂CO₃ 7,2/21,2 - 0,4/5,3 | 1:4 | H₂ | H₂O 100 | 20 | 3 | 1 | 8,4 | 10,7 | 380 |
| 16 | PtCl₂ 1,4/5,3 | A1 - Li₂CO₃ 3,6/10,6 - 0,2/2,65 | 1:2 | H₂ | H₂O 100 | 20 | 2 | 1 | 6,1 | 16,4 | 440 |
| 17 | PtCl₂ 1,4/5,3 | A1 - Li₂CO₃ 7,2/21,2 - 0,4/5,3 | 1:4 | H₂ | H₂O 100 | 20 | 1,5 | 1 | 9,5 | 10,4 | 380 |
| 18 | PtCl₂ 1,4/5,3 | A1 - LiBr 7,2/21,2-0,5/5,3 | 1:4 | H₂ | H₂O 100 | 20 | 3 | 1 | 9,7 | 9,8 | 360 |
| 19 | PtCl₂ 1,4/5,3 | A1 - LiBr 3,6/10,6 - 0,25/2,65 | 1:2 | H₂ | H₂O 100 | 20 | 3 | 1 | 6,1 | 16,9 | 370 |
| 20 | PtCl₂ 1,4/5,3 | A2 - Li₂CO₃ 11,5/42,4 - 0,8/10,6 | 1:8 | H₂ | H₂O 100 | 20 | 3 | 1 | 14,1 | 7,1 | 160 |
| 21 | PtCl₂ | A4 - Li₂CO₃ | 1:8 | H₂ | H₂O | 20 | 3 | 1 | 17,3 | 5,7 | 110 |

TABLE 6-continued

Tenside-stabilized colloid of metals of the groups VIII-Ib of the periodic system by reduction with hydrogen in $H_2O$

| No. | Metal salt g/mmole | Tenside g/mmole | Metal salt/-tenside molar ratio | Reduction agent | Solvent ml | Reaction conditions T, °C. | t,h | P,bar | isolated amount of product g | Metal content % | Water solubility in mg atom metal/l water |
|---|---|---|---|---|---|---|---|---|---|---|---|
|    | 1,4/5,3 | 14,6/42,4 - 0,8/10,6 |     |       | 100 |    |   |   |      |      |     |
| 22 | $PtCl_2$ 1,4/5,3 | B1 - $Li_2CO_3$ 21,7/21,2 -0,4/5,3 | 1:4 | $H_2$ | $H_2O$ 100 | 20 | 3 | 1 | 25,1 | 4,1 | 105 |
| 23 | $PtCl_2$ 1,4/5,3 | D1 - $Li_2CO_3$ 7/- - 0,4/5,3 | — | $H_2$ | $H_2O$ 100 | 20 | 4 | 1 | 9,5 | 10,6 | 130 |
| 24 | $Pt,Cl_2$ 1,4/5,3 | C1 - $Li_2CO_3$ 7/- -0,4/5,3 | — | $H_2$ | $H_2O$ 100 | 20 | 2 | 1 | 9,7 | 10,6 | 145 |
| 25 | $PtCl_2$ 1,4/5,3 | E1 -$Li_2CO_3$ 8,3/21 ,2 - 0,4/5,3 | 1:4 | $H_2$ | $H_2O$ 100 | 20 | 4 | 1 | 11,5 | 8,9 | 110 |
| 26 | $PtCl_2$ 1,4/5,3 | F1 - $Li_2CO_3$ 7,2/- - 0,4/5,3 | — | $H_2$ | $H_2O$ 200 | 20 | 3 | 1 | 13,7 | 8,8 | 110 |
| 27 | $PtCl_2$ 1,4/5,3 | B2 - $Li_2CO_3$ 7,2/21 ,2 - 0,4/5,3 | 1:4 | $H_2$ | $H_2O$ 100 | 20 | 3 | 1 | 10,8 | 9,1 | 105 |

What is claimed is:

1. A process for producing water-soluble, surfactant-stabilized colloids of mono- and bimetals of groups VIII and Ib of the periodic system, said colloids having particles ranging in sizes of from 1 to 10 nm, said process comprising:

a) reacting metal salts with a chemical reducing agent in the presence of a strongly hydrophilic surfactant selected from the group consisting of amphiphilic betaines, cationic surfactants, fatty alcohol polyglycol ethers, polyoxyethylene-carbohydrate-fatty alkyl esters, anionic surfactants and amphiphilic sugar surfactants, in water in the absence of an organic solvent, at a temperature between 0° C. and 100° C., at normal pressure, and optionally with the addition of an alkali carbonate and/or ammonium chloride to yield an aqueous solution comprising said colloids; and b) isolating said colloids from said aqueous solution in a concentration of >100 mg atom metal/liter.

2. A process according to claim 1, wherein the chemical reducing agent is selected from the group consisting of hydrides, hydrogen and alkali formates.

3. A process according to claim 1 or 2, wherein the strongly hydrophilic surfactant is selected from the group consisting of non-ionic surfactants having HLB-values >8.

4. Water-soluble, surfactant-stabilized colloids of mono- and bimetals of groups VIII and Ib of the periodic system, said colloids having particles ranging in sizes of from 1 to 10 nm, said colloids being covered on a surface area thereof with a strongly hydrophilic surfactant selected from the group consisting of amphiphilic betaines, cationic surfactants, fatty alcohol polyglycol ethers, polyoxyethylene-carbohydrate-fatty alkyl esters, anionic surfactants and amphiphilic sugar surfactants, and said colloids being obtainable by a process comprising:

a) reacting metal salts with a chemical reducing agent in the presence of a strongly hydrophilic surfactant selected from the group consisting of amphiphilic betaines, cationic surfactants, fatty alcohol polyglycol ethers, polyoxyethylene-carbohydrate-fatty alkyl esters, anionic surfactants and amphiphilic sugar surfactants, in water in the absence of an organic solvent, at a temperature between 0° C. and 100° C., at normal pressure, and optionally with the addition of an alkali carbonate and/or ammonium chloride to yield an aqueous solution comprising said colloids; and b) isolating said colloids from said aqueous solution in a concentration of >100 mg atom metal/liter.

5. A process for preparing a heterogeneous metal colloid catalyst comprising adsorbing mono- and bimetallic colloids according to claim 4 from aqueous solution onto inorganic or organic carrier materials.

6. A carrier supported heterogeneous metal colloid catalyst comprising mono- and bimetallic colloids according to claim 4 adsorbed from aqueous solution onto inorganic or organic carrier materials.

7. In a process comprising partially oxidizing a primary alcohol functionality in a carbohydrate in the presence of a catalyst, wherein the improvement comprises using as the catalyst a carrier supported heterogeneous metal colloid catalyst according to claim 6, wherein said carrier supported heterogeneous metal colloid catalyst is selected from the group consisting of Pt-A-activated carbon, Pd-A-carbon and Pd/Pt-A-carbon.

8. In a process comprising selectively cis-hydrogenating a carbon-carbon triple bonds in the presence of a catalyst, wherein the improvement comprises using as the catalyst a carrier supported heterogeneous metal colloid catalyst according to claim 6, wherein said carrier supported heterogeneous metal colloid catalyst is selected from the group consisting of palladium colloid-A-carbon catalysts.

9. A process according to claim 8, wherein the palladium colloid-A-carbon catalyst is selected from the group consisting of Pd-colloid-$CaCO_3$ catalysts.

10. In a process comprising selectively hydrogenating benzene to cyclohexene in the presence of a catalyst, wherein the improvement comprises using as the catalyst a carrier supported heterogeneous metal colloid catalyst according to claim 8, wherein said carrier consists of an oxide of a lanthanoid metal.

11. A process according to claim 10, wherein the carrier supported heterogeneous metal colloid catalyst is a ruthenium-lanthanodioxide-heterogeneous catalyst.

12. Colloids according to claim 4, characterized in that the strongly hydrophilic surfactants are selected from particularly non-ionic surfactants having HLB-values of >8.

13. Mono- and bimetallic colloids according to claim 4 which are from Cu, Ru, Rh, Pd, Ir, Pt, Ag, Ru/Fe, Pt/Co, Pt/Rh, Pt/Pd, Pt/Ir, Pt/Cu, Pt/Ru, Rh/ir, Rh/Ru, Ru/ir colloids, which are alkali-free stabilized hydrophilically with 3-(N,N-dimethyldodecyl ammonium)propane sulfonate, and being soluble in water at a concentration of >100 mg atom metal/l.

14. Mono- and bimetallic colloids according to claim 4 which are from Ru, Rh, Pd, Pt, Pt/Co, Pt/Ni, Pt/Ir, Pt/Cu colloids, which are hydrophilically stabilized with lauryldimethyl carboxymethyl ammonium betaine, and being soluble in water at a concentration of >100 mg atom metal/l.

15. Ru- and Pt-colloids according to claim 4, which are hydrophilically stabilized with cocoamidopropyl betaines, and being soluble in water at a concentration of >100 mg atom metal/l.

16. Platinum colloids according to claim 4, which are hydrophilically stabilized with

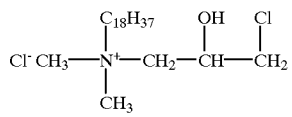

and being soluble in water at a concentration of >100 mg atom metal/l.

17. Platinum colloids according to claim 4, which are hydrophilically stabilized with

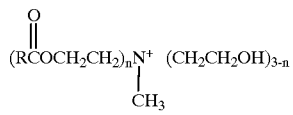

R=alkyl radical of partially hydrogenated palm grease, and being soluble in water at a concentration of >100 mg atom metal/l.

18. Mono- and bimetallic colloids according to claim 4 which are from Ni, Co, Pt, Pt/Pd colloids which are hydrophilically stabilized with polyoxyethylene laurylether, and being soluble in water at a concentration of >100 mg atom metal/l.

19. Platinum colloids according to claim 4, which are hydrophilically stabilized with polyoxyethylene sorbitan monolaurat, and being soluble in water at a concentration of >100 mg atom metal/l.

20. Platinum colloids according to claim 4, which are hydrophilically stabilized with Na-cocoamidoethyl-N-hydroxy-ethyl-glucinate, and being soluble in water at a concentration of >100 mg atom metal/l.

21. Platinum colloids according to claim 4, which are hydrophilically stabilized with alkylpolyglycoside, and being soluble in water at a concentration of >100 mg atom metal/l.

22. Process according to claim 5, wherein the metal colloids have concentrations of up to 25 percent per weight of metal content in relation to the total weight of the solution.

23. Catalysts according to claim 6, characterized in that the carrier materials comprise carbon carriers, ceramic oxides, carbonates, sulfates or zeolites in the form of powders or formed bodies.

24. Catalysts according to claim 2 characterized by a coverage comprising oxides of lanthanoide elements, in particular lanthanum oxide.

25. In a process comprising selectively cis-hydrogenating a carbon triple bond in the presence of a catalyst, wherein the improvement comprises using as the catalyst a carrier supported heterogeneous metal colloid according to claim 6, wherein said carrier supported hetergeneous metal colloid catalyst is selected from the group consisting of palladium colloid—$CaCO_3$ catalysts.

* * * * *